United States Patent [19]

Burke et al.

[11] Patent Number: 4,895,976

[45] Date of Patent: Jan. 23, 1990

[54] PREPARATION OF 4-PENTANOATES BY ISOMERIZATION

[75] Inventors: Patrick M. Burke; Norman Herron, both of Wilmington; Stephan J. McLain, Hockessin, all of Del.

[73] Assignee: E. I. Du Pont de Nemours and Company, Wilmington, Del.

[21] Appl. No.: 197,221

[22] Filed: May 23, 1988

[51] Int. Cl.$^4$ ............................................. C07C 67/30
[52] U.S. Cl. .................................... 560/211; 560/217
[58] Field of Search ................................ 560/211, 217

[56] References Cited

FOREIGN PATENT DOCUMENTS 3521380 12/1986 Fed. Rep. of Germany .
3521381 12/1986 Fed. Rep. of Germany .

*Primary Examiner*—Paul J. Killos

[57] ABSTRACT

Isomerization of 3-pentenoate esters to 4-pentenoate esters using homogeneous or heterogeneous catalysts of zero valent nickel complexes with an acid promoter.

5 Claims, No Drawings

PREPARATION OF 4-PENTANOATES BY ISOMERIZATION

FIELD OF THE INVENTION

This invention relates to the selective isomerization of 3-pentenoate esters to form the corresponding 4-pentenoate esters by use of zero valent nickel complexes and an acid promoter.

BACKGROUND OF THE INVENTION

Drinkard et al. U.S. Pat. No. 3,538,142 disclose a process for isomerizing 3-pentenenitrile to 4-pentenenitrile using nickel hydride coordination compounds prepared from zero valent nickel complexes and an acid.

Schneider et al. U.S. Pat. No. 4,527,815 disclose the preparation of 4-pentenoates by the isomerization at elevated temperatures of 3-pentenoates using an acidic ion-exchange resin or acidic zeolite containing a noble metal of group 8 of the periodic table as a catalyst.

Hoeldrich et al. German Preliminary Published Application DE 3521 380 A1 disclose the synthesis of 4-pentenoic acid methyl ester by contacting 3-pentenoic acid methyl ester with Y zeolites containing cobalt in a +2 oxidation state and an alkali or alkaline earth metal.

The isomerization of methyl-3-pentenoate to methyl-4-pentenoate at elevated temperature using a pentasil zeolite without a metal promoter is also disclosed by Hoeldrich et al. in German Preliminary Published Application DE No. 3521 381 A1.

In pending U.S. application Ser. No. 48,651 the preparation of 4-pentenoates by isomerization of 3-pentenoates with perfluorinated ion-exchange catalysts is described. Pending U.S. application Ser. No. 57,433 describes the isomerization of 3-pentenenitriles to 4-pentenenitriles with heterogeneous catalysts containing noble metals of group 8 of the periodic table.

SUMMARY OF THE INVENTION

The present invention is a process for the preparation of 4-pentenoic esters, i.e., a compound having the formula $CH_2=CH-CH_2-CH_2-CO_2R$ where R is alkyl of 1–8 carbon atoms, by the isomerization at elevated temperatures, about 80° to 200° C., of the corresponding 3-pentenoic ester, i.e., a compound having the formula $CH_3-CH=CH-CH_2-CO_2R$ where R is alkyl of 1–8 carbons with a catalyst of a zero valent nickel complex and an acid The reaction is usually substantially complete in an hour or less. The reaction may be carried out at pressures of about 15 psig to about 200 psig.

In a preferred embodiment, the zero valent nickel catalyst is a Ni(0) phosphite or a Ni(0) carbonyl complex and the acid is an acid exchanged Y-zeolite, an acidic amorphous silica-aluminate, sulfuric acid or trifluoromethylsulfonic acid.

The catalyst may be a homogeneous catalyst or a heterogeneous catalyst When the catalyst is a homogeneous catalyst it is believed to have the formula $HNi(PYZ)_n+X-$.

The process of the present invention is particularly effective in the isomerization of methyl-3-pentenoate to methyl-4-pentenoate.

The finding that the much less expensive Ni catalysts are both highly active and highly selective for the isomerization of 3-pentenoates to 4-pentenoates solves a major problem posed by the use of the expensive noble metal catalysts of the prior art The 4-pentenoates are key intermediates in various routes to both adipic acid and caprolactam from butadiene.

DETAILED DESCRIPTION

The nickel catalysts used in the present invention are prepared from a suitable zero valent nickel complex and an acid promoter. Suitable zero valent nickel complexes are nickel tetracarbonyl, $Ni(CO)_4$, bis(1,5-cyclooctadiene)nickel(0), $Ni(COD)_2$, tetrakis(triphenylphosphite)nickel(0), $[(C_6H_5O)_3P]_4Ni$, tetrakis(trimethylphosphite)nickel(0), $[(CH_3O)_3P]_4Ni$, and bis(triphenylphosphite)nickel dicarbonyl, $[(C_6H_5O)_3P]_2Ni(CO)_2$. The phosphite containing zero valent nickel complexes may be prepared in-situ from a suitable zero valent nickel precursor, e.g., $Ni(COD)_2$, and the free phosphite in stoichiometric amount or in up to 10 fold excess of stoichiometric amount.

The acid promoter may be a heterogeneous acid or a strong homogeneous acid i.e., one with a Hammett acidity value, $H_0$, of less than $-8$, and trifluoroacetic acid. Suitable heterogeneous acids are acid exchanged Y-zeolites and acidic amorphous silica-aluminates. Suitable homogeneous acids are concentrated sulfuric acid, fluorosulfonic acid, hexafluorophosphoric acid, methylsulfonic acid, trifluoromethylsulfonic acid and trifluoroacetic acid. Hammett Acidity is discussed in "Mechanism and Theory of Organic Chemistry" T. H. Lowry and K. S. Richardson, Harper & Row, New York 1976, page 130.

The active homogeneous catalysts may be prepared in-situ by mixing the zero valent nickel complex and acid. Preferably the acid and nickel complex are present in at least equivalent amounts but higher ratios of acid to nickel (up to 10 to 1) may also be utilized.

When the catalyst is a homogeneous catalyst, it is believed to be a nickel hydride complex of the formula: $HNi(PYZ)_n+X-$ where P is phosphorus, Z is selected from the class consisting of $R'$ and $OR'$ wherein $R'$ is selected from the class consisting of hydrocarbyl radicals of up to 18 carbon atoms—Cl—, —O—, and CN, and Y is selected from the class consisting of substituted with groups selected from the class consisting of —Cl, —O—, and —CN, and Y is selected from the class consisting of two Z's and groups of the formula —$R''$— and —O—$R''$—O—wherein —$R''$—is a hydrocarbylene radical of from 2 to 12 carbon atoms and wherein n is in integer, namely 3 or 4 and X— is an anion of a strong homogeneous acid.

The heterogeneous nickel catalysts may be prepared by impregnating a solid acid e.g., a fully acid exchanged Y zeolite, with a zero valent nickel complex optionally followed by a mild ($<100°$ C.) heat treatment. Preferentially, the catalyst is prepared in two steps by first treating the solid acid with a phosphorus-free zero valent nickel complex e.g., Ni(COD): or $Ni(CO)_4$, and then treating the resulting solid complex with an organic solvent solution of the phosphorus ligand e.g., triphenylphosphite, followed by filtering and drying at ambient temperature to about 50° C. The nickel loading on the solid acid is in the range 0.015 to 1.5 milliequivalents per gram (meq/g) of dry solid acid with the preferred Ni concentration being in the range 0.15 to 1.0 meq/g. Although the presence of a phosphorus ligand is not essential for isomerization activity, higher selectivity is obtained with certain phosphorus ligands. The preferred phosphorus ligand is triphenylphosphite and the preferred P/Ni ratio is 4 to 5, although P/Ni ratios of 1:1 to 10:1 can be used.

The isomerization reaction is carried out by contacting the 3-pentenoate, alone or dissolved in a suitable inert solvent such as toluene and trimethylbenzene, at elevated temperature, in the range 80° C. to 200° C. and preferentially in the range 120° C. to 140° C. The contact time is important; it will depend on the activity of the catalyst and the amount of catalyst used. Highly active catalysts will form 7-8 mole % 4-pentenoate isomer from 100% 3-pentenoate in less than 1 minute with as little as 0.001 moles of Ni per mole of 3-pentenoate. With these very active catalysts longer contact times or higher Ni to pentenoate isomer ratios are undesirable since too much of the undesirable 2-pentenoate isomer is formed under these conditions. With less active catalysts contact times of one hour or more may be employed.

In the following examples which illustrate the invention and compare the invention to the art, all parts and percentages are in parts by weight and all temperatures are in degrees centigrade.

CATALYST PREPARATION

Catalyst A ("HY/Ni(COD)$_2$.5P(OPh)$_3$")

The acid form of Y-zeolite ("HY") was prepared by heating Linde NH$_4$Y zeolite (LZY-82, Union Carbide) from 25° C. to 350° C. in high vacuum over a period of 5 hours. (Below this material is referred to as, catalyst A1). The dehydrated zeolite was then transferred to a nitrogen filled drybox. To a slurry of the HY zeolite (1.0 gram) in pentane (50 ml) was added bis(1,5-cyclooctadiene) nickel(0) (0.136 grams; 0.2 mmoles). On stirring the mixture at ambient temperature for 3.5 hours a dark red-brown solid was obtained. To this slurry was added dropwise over a period of 5 minutes a solution of triphenylphosphite (0.310 grams; 1.0 mmole) in 5 ml pentane. The mixture was stirred for 14 hours, filtered and the solid was dried in vacuo for 5 minutes at ambient temperature.

Catalyst B ("HY/Ni(COD)$_2$.5P(OCH$_3$)")

This catalyst was prepared in a manner similar to that of catalyst A except that the amount of Ni(COD)$_2$ was reduced to 0.125 mmoles per gram of HY and trimethylphosphite (5 equivalents per equivalent of Ni) was substituted for triphenylphosphite.

Catalyst C ("HY/Ni(CO)$_4$")

The HY zeolite was prepared by heating NH$_4$Y zeolite to 400° C. in flowing dry oxygen for 2 hours, holding at 400° C. for an additional 2 hours and cooling in a drybox under nitrogen at −10° C. A mixture of 10 grams of the HY and 0.5 grams Ni(CO)$_4$ was equilibrated at −10° C. for 14 hours. The resulting nickel containing zeolite was heated in vacuo at 50° C. for 1 hour. Analysis of the resulting light gray solid showed 1.72% Ni and 9.77% Al.

Catalyst D ("HY/Ni(CO)$_4$.(C$_2$H$_5$O)$_3$P")

To 5 grams of catalyst C in a drybox under nitrogen was added 10 ml of triethylphosphite. The resulting mixture was equilibrated at −10° C. for 14 hours. It was then filtered, washed with methylene chloride to remove excess phosphite and dried in vacuo for 1 hour. Analysis showed 0.5% Ni and 3.3% P.

EXAMPLE 1

To trans-methyl-3-pentenoate (M3P; 10.0 grams) at 135° C. under a nitrogen purge was added 1.0 grams of catalyst A. Samples of the liquid were taken at intervals and analyzed for pentenoate isomers by gas chromatography on a 26M×0.22 mm Chrompack CP-WAX-57 capillary GC column. The following results were obtained:

| Time (Min) | % M4P | % M2P | Selectivity (% M4P/% M2P) |
|---|---|---|---|
| 0 | 0 | 0.82 | — |
| 1 | 2.06 | 0.97 | 14.3 |
| 5 | 4.70 | 1.08 | 18.2 |
| 10 | 5.64 | 1.13 | 18.4 |
| 30 | 6.31 | 1.36 | 11.8 |
| 60 | 6.70 | 1.29 | 14.3 |

M4P = methyl-4-pentenoate
M2P = cis and trans-methyl-2-pentenoate

In this and the following examples the selectivity is defined as the number of moles of 4-pentenoate formed to the number of moles of 2-pentenoate (cis and trans isomers) formed during the isomerization. A correction is made for the 2-pentenoates present initially.

EXAMPLES 2 to 5

The procedure in Example 1 was repeated except that catalysts A1, B, C, D, were substituted for Catalyst A. The result obtained are summarized in the following table:

| Example | Catalyst | Time at 135° C.(min) | % M4P | Selectivity (% M4P/% M2P) |
|---|---|---|---|---|
| 2 (control) | A1 | 5 | 0.9 | 1.5 |
|  |  | 30 | 2.7 | 1.4 |
| 3 | B | 5 | 3.6 | 7.0 |
|  |  | 30 | 4.8 | 3.3 |
| 4 | C | 5 | 4.2 | 6.1 |
|  |  | 30 | 5.3 | 2.7 |
| 5 | D | 5 | 3.8 | 4.0 |
|  |  | 30 | 4.3 | 3.4 |

The results show that addition of zero valent nickel leads to a large increase in both activity and selectivity compared with the HY-zeolite control (catalyst A1).

CONTROL EXAMPLE A

For comparison with the above, NH$_4$Y zeolite was exchanged with nickel in its +2 oxidation state (form nickel (II) acetate) and calcined in oxygen at 400° C. to convert it to the acid form. Various concentrations of evaluated for activity and selectivity in the isomerization of M3P to M4P as described in Example 1. The result are summarized below:

| Catalyst | % Nickel | % M4P (30 min) | Selectivity (M4P/M2P) |
|---|---|---|---|
| E | 0.25 | 2.60 | 1.1 |
| F | 0.75 | 1.83 | 1.3 |
| G | 2.0 | 0.93 | 0.68 |
| H | 4.0 | 0.79 | 0.60 |

The results show that substitution of Ni(II) into the zeolite does not increase (and in fact decreases) its activity or selectivity for the isomerization of M3P Similar results were obtained when Co(II) was substituted for Ni(II) in the above series.

PREPARATION OF 4-PENTANOATES BY ISOMERIZATION

FIELD OF THE INVENTION

This invention relates to the selective isomerization of 3-pentenoate esters to form the corresponding 4-pentenoate esters by use of zero valent nickel complexes and an acid promoter.

BACKGROUND OF THE INVENTION

Drinkard et al. U.S. Pat. No. 3,538,142 disclose a process for isomerizing 3-pentenenitrile to 4-pentenenitrile using nickel hydride coordination compounds prepared from zero valent nickel complexes and an acid.

Schneider et al. U.S. Pat. No. 4,527,815 disclose the preparation of 4-pentenoates by the isomerization at elevated temperatures of 3-pentenoates using an acidic ion-exchange resin or acidic zeolite containing a noble metal of group 8 of the periodic table as a catalyst.

Hoeldrich et al. German Preliminary Published Application DE 3521 380 A1 disclose the synthesis of 4-pentenoic acid methyl ester by contacting 3-pentenoic acid methyl ester with Y zeolites containing cobalt in a +2 oxidation state and an alkali or alkaline earth metal.

The isomerization of methyl-3-pentenoate to methyl-4-pentenoate at elevated temperature using a pentasil zeolite without a metal promoter is also disclosed by Hoeldrich et al. in German Preliminary Published Application DE No. 3521 381 A1.

In pending U.S. application Ser. No. 48,651 the preparation of 4-pentenoates by isomerization of 3-pentenoates with perfluorinated ion-exchange catalysts is described. Pending U.S. application Ser. No. 57,433 describes the isomerization of 3-pentenenitriles to 4-pentenenitriles with heterogeneous catalysts containing noble metals of group 8 of the periodic table.

SUMMARY OF THE INVENTION

The present invention is a process for the preparation of 4-pentenoic esters, i.e., a compound having the formula $CH_2=CH-CH_2-CH_2-CO_2R$ where R is alkyl of 1-8 carbon atoms, by the isomerization at elevated temperatures, about 80° to 200° C., of the corresponding 3-pentenoic ester, i.e., a compound having the formula $CH_3-CH=CH-CH_2-CO_2R$ where R is alkyl of 1-8 carbons with a catalyst of a zero valent nickel complex and an acid The reaction is usually substantially complete in an hour or less. The reaction may be carried out at pressures of about 15 psig to about 200 psig.

In a preferred embodiment, the zero valent nickel catalyst is a Ni(0) phosphite or a Ni(0) carbonyl complex and the acid is an acid exchanged Y-zeolite, an acidic amorphous silica-aluminate, sulfuric acid or trifluoromethylsulfonic acid.

The catalyst may be a homogeneous catalyst or a heterogeneous catalyst When the catalyst is a homogeneous catalyst it is believed to have the formula $HNi(PYZ)_n + X-$.

The process of the present invention is particularly effective in the isomerization of methyl-3-pentenoate to methyl-4-pentenoate.

The finding that the much less expensive Ni catalysts are both highly active and highly selective for the isomerization of 3-pentenoates to 4-pentenoates solves a major problem posed by the use of the expensive noble metal catalysts of the prior art The 4-pentenoates are key intermediates in various routes to both adipic acid and caprolactam from butadiene.

DETAILED DESCRIPTION

The nickel catalysts used in the present invention are prepared from a suitable zero valent nickel complex and an acid promoter. Suitable zero valent nickel complexes are nickel tetracarbonyl, $Ni(CO)_4$, bis(1,5-cyclooctadiene)nickel(0), $Ni(COD)_2$, tetrakis(triphenylphosphite)nickel(0), $[(C_6H_5O)_3P]_4Ni$, tetrakis(trimethylphosphite)nickel(0), $[(CH_3O)_3P]_4Ni$, and bis(triphenylphosphite)nickel dicarbonyl, $[(C_6H_5O)_3P]_2Ni(CO)_2$. The phosphite containing zero valent nickel complexes may be prepared in-situ from a suitable zero valent nickel precursor, e.g., $Ni(COD)_2$, and the free phosphite in stoichiometric amount or in up to 10 fold excess of stoichiometric amount.

The acid promoter may be a heterogeneous acid or a strong homogeneous acid i.e., one with a Hammett acidity value, $H_0$, of less than $-8$, and trifluoroacetic acid. Suitable heterogeneous acids are acid exchanged Y-zeolites and acidic amorphous silica-aluminates. Suitable homogeneous acids are concentrated sulfuric acid, fluorosulfonic acid, hexafluorophosphoric acid, methylsulfonic acid, trifluoromethylsulfonic acid and trifluoroacetic acid. Hammett Acidity is discussed in "Mechanism and Theory of Organic Chemistry" T. H. Lowry and K. S. Richardson, Harper & Row, New York 1976, page 130.

The active homogeneous catalysts may be prepared in-situ by mixing the zero valent nickel complex and acid. Preferably the acid and nickel complex are present in at least equivalent amounts but higher ratios of acid to nickel (up to 10 to 1) may also be utilized.

When the catalyst is a homogeneous catalyst, it is believed to be a nickel hydride complex of the formula: $HNi(PYZ)_n + X-$ where P is phosphorus, Z is selected from the class consisting of R' and OR' wherein R' is selected from the class consisting of hydrocarbyl radicals of up to 18 carbon atoms—Cl—, —O—, and CN, and Y is selected from the class consisting of substituted with groups selected from the class consisting of —Cl, —O—, and —CN, and Y is selected from the class consisting of two Z's and groups of the formula —R"— and —O—R"—O—wherein —R"—is a hydrocarbylene radical of from 2 to 12 carbon atoms and wherein n is in integer, namely 3 or 4 and X— is an anion of a strong homogeneous acid.

The heterogeneous nickel catalysts may be prepared by impregnating a solid acid e.g., a fully acid exchanged Y zeolite, with a zero valent nickel complex optionally followed by a mild (<100° C.) heat treatment. Preferentially, the catalyst is prepared in two steps by first treating the solid acid with a phosphorus-free zero valent nickel complex e.g., Ni(COD): or $Ni(CO)_4$, and then treating the resulting solid complex with an organic solvent solution of the phosphorus ligand e.g., triphenylphosphite, followed by filtering and drying at ambient temperature to about 50° C. The nickel loading on the solid acid is in the range 0.015 to 1.5 milliequivalents per gram (meq/g) of dry solid acid with the preferred Ni concentration being in the range 0.15 to 1.0 meq/g. Although the presence of a phosphorus ligand is not essential for isomerization activity, higher selectivity is obtained with certain phosphorus ligands. The preferred phosphorus ligand is triphenylphosphite and the preferred P/Ni ratio is 4 to 5, although P/Ni ratios of 1:1 to 10:1 can be used.

The isomerization reaction is carried out by contacting the 3-pentenoate, alone or dissolved in a suitable inert solvent such as toluene and trimethylbenzene, at elevated temperature, in the range 80° C. to 200° C. and preferentially in the range 120° C. to 140° C. The contact time is important; it will depend on the activity of the catalyst and the amount of catalyst used. Highly active catalysts will form 7–8 mole % 4-pentenoate isomer from 100% 3-pentenoate in less than 1 minute with as little as 0.001 moles of Ni per mole of 3-pentenoate. With these very active catalysts longer contact times or higher Ni to pentenoate isomer ratios are undesirable since too much of the undesirable 2-pentenoate isomer is formed under these conditions. With less active catalysts contact times of one hour or more may be employed.

In the following examples which illustrate the invention and compare the invention to the art, all parts and percentages are in parts by weight and all temperatures are in degrees centigrade.

CATALYST PREPARATION

Catalyst A ("HY/Ni(COD)₂.5P(OPh)₃")

The acid form of Y-zeolite ("HY") was prepared by heating Linde NH$_4$Y zeolite (LZY-82, Union Carbide) from 25° C. to 350° C. in high vacuum over a period of 5 hours. (Below this material is referred to as, catalyst A1). The dehydrated zeolite was then transferred to a nitrogen filled drybox. To a slurry of the HY zeolite (1.0 gram) in pentane (50 ml) was added bis(1,5-cyclooctadiene) nickel(0) (0.136 grams; 0.2 mmoles). On stirring the mixture at ambient temperature for 3.5 hours a dark red-brown solid was obtained. To this slurry was added dropwise over a period of 5 minutes a solution of triphenylphosphite (0.310 grams; 1.0 mmole) in 5 ml pentane. The mixture was stirred for 14 hours, filtered and the solid was dried in vacuo for 5 minutes at ambient temperature.

Catalyst B ("HY/Ni(COD)₂.5P(OCH₃)")

This catalyst was prepared in a manner similar to that of catalyst A except that the amount of Ni(COD), was reduced to 0.125 mmoles per gram of HY and trimethylphosphite (5 equivalents per equivalent of Ni) was substituted for triphenylphosphite.

Catalyst C ("HY/Ni(CO)₄")

The HY zeolite was prepared by heating NH$_4$Y zeolite to 400° C. in flowing dry oxygen for 2 hours, holding at 400° C. for an additional 2 hours and cooling in a drybox under nitrogen at −10° C. A mixture of 10 grams of the HY and 0.5 grams Ni(CO)$_4$ was equilibrated at −10° C. for 14 hours. The resulting nickel containing zeolite was heated in vacuo at 50° C. for 1 hour. Analysis of the resulting light gray solid showed 1.72% Ni and 9.77% Al.

Catalyst D ("HY/Ni(CO)₄.(C₂H₅O)₃P")

To 5 grams of catalyst C in a drybox under nitrogen was added 10 ml of triethylphosphite. The resulting mixture was equilibrated at −10° C. for 14 hours. It was then filtered, washed with methylene chloride to remove excess phosphite and dried in vacuo for 1 hour. Analysis showed 0.5% Ni and 3.3% P.

EXAMPLE 1

To trans-methyl-3-pentenoate (M3P; 10.0 grams) at 135° C. under a nitrogen purge was added 1.0 grams of catalyst A. Samples of the liquid were taken at intervals and analyzed for pentenoate isomers by gas chromatography on a 26M×0.22 mm Chrompack CP-WAX-57 capillary GC column. The following results were obtained:

| Time (Min) | % M4P | % M2P | Selectivity (% M4P/% M2P) |
|---|---|---|---|
| 0 | 0 | 0.82 | — |
| 1 | 2.06 | 0.97 | 14.3 |
| 5 | 4.70 | 1.08 | 18.2 |
| 10 | 5.64 | 1.13 | 18.4 |
| 30 | 6.31 | 1.36 | 11.8 |
| 60 | 6.70 | 1.29 | 14.3 |

M4P = methyl-4-pentenoate
M2P = cis and trans-methyl-2-pentenoate

In this and the following examples the selectivity is defined as the number of moles of 4-pentenoate formed to the number of moles of 2-pentenoate (cis and trans isomers) formed during the isomerization. A correction is made for the 2-pentenoates present initially.

EXAMPLES 2 to 5

The procedure in Example 1 was repeated except that catalysts A1, B, C, D, were substituted for Catalyst A. The result obtained are summarized in the following table:

| Example | Catalyst | Time at 135° C.(min) | % M4P | Selectivity (% M4P/% M2P) |
|---|---|---|---|---|
| 2 (control) | A1 | 5 | 0.9 | 1.5 |
|  |  | 30 | 2.7 | 1.4 |
| 3 | B | 5 | 3.6 | 7.0 |
|  |  | 30 | 4.8 | 3.3 |
| 4 | C | 5 | 4.2 | 6.1 |
|  |  | 30 | 5.3 | 2.7 |
| 5 | D | 5 | 3.8 | 4.0 |
|  |  | 30 | 4.3 | 3.4 |

The results show that addition of zero valent nickel leads to a large increase in both activity and selectivity compared with the HY-zeolite control (catalyst A1).

CONTROL EXAMPLE A

For comparison with the above, NH$_4$Y zeolite was exchanged with nickel in its +2 oxidation state (form nickel (II) acetate) and calcined in oxygen at 400° C. to convert it to the acid form. Various concentrations of evaluated for activity and selectivity in the isomerization of M3P to M4P as described in Example 1. The result are summarized below:

| Catalyst | % Nickel | % M4P (30 min) | Selectivity (M4P/M2P) |
|---|---|---|---|
| E | 0.25 | 2.60 | 1.1 |
| F | 0.75 | 1.83 | 1.3 |
| G | 2.0 | 0.93 | 0.68 |
| H | 4.0 | 0.79 | 0.60 |

The results show that substitution of Ni(II) into the zeolite does not increase (and in fact decreases) its activity or selectivity for the isomerization of M3P Similar results were obtained when Co(II) was substituted for Ni(II) in the above series.

EXAMPLE 6

To 5.0 grams methyl-3-pentenoate at 135° C. was added 0.29 grams of tetrakis(triphenylphosphite) Nickel(0) (0.224 milliequivalents of Ni) and 12.5 μl (0.14 meq) trifluoromethylsulfonic acid. Samples were taken at intervals and analyzed for pentenoate esters as in example 1. The following results were obtained.

| Time (min) | % M4P | % M2P | Selectivity (M4P/M2P) |
|---|---|---|---|
| 0 | 0.0 | 0.82 | — |
| 1 | 7.47 | 1.59 | 9.71 |
| 3 | 7.53 | 1.60 | 9.70 |
| 10 | 7.52 | 1.65 | 9.08 |

The results show that this homogeneous nickel catalyst has high activity and selectivity for the isomerization of M3P to M4P.

EXAMPLE 7

To 5.0 grams methyl-3-pentenoate at 135° C. was added 0.04 grams (0.056 meq) tetrakis(triethylphosphite) nickel(0) and 5 μl trifluoromethylsulfonic acid Samples taken at time intervals showed the following analyses:

| Time (Min) | % M4P | % M2P | Selectivity (M4P/M2P) |
|---|---|---|---|
| 0 | 0.0 | 0.82 | — |
| 1 | 7.77 | 7.51 | 1.2 |
| 3.0 | 8.18 | 9.19 | 1.0 |
| 5.0 | 8.34 | 9.98 | 0.9 |

This catalyst shows very high activity for the isomerization.

CONTROL EXAMPLE 7A

The above experiment was repeated except that the acid was omitted. Product analysis showed that no M4P was formed in up to 60 minutes at 135° C. This demonstrates that an acid promoter is necessary to activate the Ni(0) complex.

EXAMPLE 8

To 5.0 grams of methyl-3-pentenoate at 135° C. was added 0.73 grams (0.56 meq) of tetrakis(triphenylphosphite) nickel(0) and 0.26 grams (2.24 meq) of trifluoroacetic acid. Samples taken at intervals gave the following isomer distributions:

| Time (min) | % M4P | % M2P | Selectivity (M4P/M2P) |
|---|---|---|---|
| 0 | 0 | 0.82 | — |
| 1 | 1.92 | 1.54 | 2.7 |
| 5 | 2.32 | 1.69 | 2.7 |
| 30 | 2.92 | 2.00 | 2.5 |

EXAMPLE 9

To 5.0 grams of methyl-3-pentenoate at 135° C. added 0.11 grams (2.24 meq) 96% sulfuric acid and 0.40 grams (0.56 meq) tetrakis(triethylphosphite)nickel(0). Samples taken at intervals gave the following isomer distributions:

| Time (min) | % M4P | % M2P | Selectivity (M4P/M2P) |
|---|---|---|---|
| 0 | 0 | 0.82 | — |
| 1 | 8.10 | 14.28 | 0.60 |
| 5 | 8.29 | 17.78 | 0.49 |
| 30 | 8.25 | 19.83 | 0.43 |

EXAMPLE 10

Ni(0) on amorphous Silica-Alumina
Catalyst Preparation
Ni(0) on acid enhanced Si/Al with phosphite treatment.

10 g of commercial amorphous aluminosilicate from Davison Chemical Co. containing 13 wt % alumina was slurried in 1000 ccs water. The pH of the slurry was adjusted to 1 with concentrated HCl and then stirred for 30 minutes at room temperature. After filtration and washing with 1000 ccs distilled water the powder was dried in flowing oxygen (30 ccs/min) at atmospheric pressure by ramping the temp from room to 400° C. over 4 hours. The powder was finally dried by evacuating at 400° C. for 1 further hour, sealed then transported into a dry nitrogen dry box. Here the sample was chilled to −20° C. prior to addition of 0.5 g tetracarbonylnickel. The container was tightly capped and wrapped in aluminum foil for equilibration at −20° C. for 16 hours. 1 ml of triethylphosphite was added and mixed well and then allowed to stand at room temperature for 1 hour with occasional mixing. The sample was removed from the dry box in a sealed tube furnace tube and evacuated to high vacuum on a vacuum line. The sample was heated to 50° C. for 1 hour in high vacuum during which time it turned grey. The sample was then sealed, returned to the glove box and tightly capped in separate 1 g portions for catalyst testing.

10.0 g methyl-3-pentenoate was heated to 135° C. under nitrogen. A sample taken after 5 minutes at 135° C. showed 99.2% M3P, 0.8 % TM2P and no M4P. To this was added 2 gram of the above amorphous silica-aluminate nickel catalyst. Samples taken after 1 and 5 minutes gave the following results.

| Time (min) | % M4P | % M2P | Selectivity (% M4P/M2P) |
|---|---|---|---|
| 0 | 0 | 0.8 | — |
| 1 | 1.56 | 0.9 | 17.2 |
| 5 | 6.58 | 2.09 | 5.14 |

The results show that catalyst prepared from an amorphous support and Ni(0) has high activity for the selective isomerization of M3P to M4P.

EXAMPLE 11

Homogeneous Ni(0) containing carbonyl groups

To 10.0 grams M3P at 135° C. under nitrogen was added in sequence 68 mg trifluoromethylsulfonic acid (0.448 meq H+) and 0.60 grams bis(triphenylphosphite) nickel dicarbonyl (0.448 meq Ni). Samples taken after 5, 30 and 60 minutes gave the following results.

| Time (min) | % M4P | % M2P | Selectivity (% M4P/% M2P) |
|---|---|---|---|
| 0 | 0 | 0.77 | — |
| 5 | 1.08 | 0.98 | 5.45 |
| 30 | 5.24 | 1.15 | 14.29 |

-continued

| Time (min) | % M4P | % M2P | Selectivity (% M4P/% M2P) |
|---|---|---|---|
| 60 | 7.44 | 1.35 | 13.06 |

The data show that M4P is formed more rapidly than M2P with this catalyst system.

We claim:

1. A process for the isomerization of a compound having the formula $CH_3—CH=CH—CH_2—CO_2R$ where R is alkyl of 1 to 8 carbon atoms, which comprises contacting said compound with a zero valent nickel complex with an acid promoter, at a temperature in the range of 80 to 200 degrees C. for a time up to about one hour at a pressure in the range of about 15 psig to 200 psig, and recovering a compound having the formula: $CH_2=CH—CH_2—CH_2—CO_2R$.

2. A process for the isomerization of a compound having the formula: $CH_3—CH=CH—CH_2—CO_2R$ where R is alkyl of 1 to 8 carbon atoms, which comprises contacting said compound with a nickel hydride complex of the formula $HNi(PYZ)_n + X-$ where P is phosphorus, Z is selected from the class consisting of R' and OR' wherein R' is selected from the class consisting of hydrocarbyl radicals of up to 18 carbon atoms and hydrocarbyl radicals of up to 18 carbon atoms substituted with groups selected from the class consisting of and hydrocarbyl radicals of up to 18 carbon atoms two Z's and the groups of the formula —R"— consisting and —O—R'—O— wherein —R"— is a hydrocarbylene radical of from 2 to 12 carbon atoms and wherein n is an integer, namely 3 or 4, and X— is an anion of a strong homogeneous acid or a heterogeneous acid, at a temperature in the range of 80 to 200 degrees C. for a time up to about one hour at a pressure in the range of about 15 to 200 psig, and recovering a compound having the formula $CH_2=CH_2—CH_2—CH_2—CO_2—R$.

3. The process of claim 2 in which the compound to be isomerized is methyl-3-pentenoate.

4. The process of claim 2 in which the anion is derived from a heterogeneous acid selected from the group consisting of acid exchanged y-zeolites and acidic amorphous silica-aluminates.

5. The process of claim 2 in which the anion is derived from an acid selected from the group consisting of sulfuric acid, fluorosulfonic acid, hexafluorophosphoric acid, methylsulfonic acid, trifluoromethylsulfonic acid and trifluoroacetic acid.

* * * * *